United States Patent [19]

Lewis et al.

[11] 4,167,502

[45] Sep. 11, 1979

[54] CARBOXYLIC POLYMERIC THICKENERS

[75] Inventors: Sheldon N. Lewis, Willow Grove; John J. Miller, Warminster, both of Pa.

[73] Assignee: Rohm and Haas Company, Philadelphia, Pa.

[21] Appl. No.: 857,073

[22] Filed: Dec. 5, 1977

Related U.S. Application Data

[62] Division of Ser. No. 312,433, Dec. 6, 1972, Pat. No. 4,085,167.

[51] Int. Cl.$^2$ .................. C08F 220/06; C08F 222/02; C08L 33/02
[52] U.S. Cl. .......................... 260/29.6 H; 260/29.1 R; 526/317
[58] Field of Search ...................... 260/29.1 R, 29.6 H; 526/317

[56] References Cited

U.S. PATENT DOCUMENTS

| | | | |
|---|---|---|---|
| 3,932,560 | 1/1976 | Franklin et al. | 260/29.6 H |
| 3,960,584 | 6/1976 | Savage | 260/29.6 H |
| 4,024,099 | 5/1977 | Franklin et al. | 260/29.6 H |
| 4,059,552 | 11/1977 | Zweigle et al. | 260/29.6 H |

*Primary Examiner*—Harry Wong, Jr.
*Attorney, Agent, or Firm*—Harold L. Greenwald; William E. Lambert, III

[57] ABSTRACT

Polymers of a polymerizable mixture comprising an ethylenically unsaturated acid and an oligomer of an allyl-containing ester of acrylic acid or methacrylic acid are useful as thickening and bodying agents when partially or completely neutralized.

12 Claims, No Drawings

CARBOXYLIC POLYMERIC THICKENERS

CROSS REFERENCE TO RELATED APPLICATION

This is a division of application Ser. No. 312,433 filed Dec. 6, 1972 now U.S. Pat. No. 4,085,167 issued Apr. 18, 1978.

This invention relates to certain novel polymers, to methods of making the polymers, to compositions comprising the polymers, and to the use of the polymers as thickening and bodying agents.

According to the invention, a new class of carboxylic polymers is obtained when at least one monoethylenically $\alpha,\beta$-unsaturated carboxylic acid is copolymerized with at least one oligomer of an allyl-containing ester of acrylic or methacrylic acid. These polymers, which contain a plurality of carboxylic acid groups, are particularly useful as thickening agents when partially or completely neutralized in solution or suspension.

A wide variety of monoethylenically $\alpha,\beta$-unsaturated carboxylic acids can be used in making the polymers of the present invention, and substantially any such acid which will copolymerize with the allyl-containing ester will be suitable. Among the useful acids are acrylic acid, methacrylic acid, ethacrylic acid, $\alpha$-chloroacrylic acid, crotonic acid, itaconic acid, maleic acid, fumaric acid, citraconic acid, mesaconic acid, and the like. Mixtures of these acids can also be employed. In a preferred embodiment of the invention, the acid is acrylic acid.

The allyl-containing oligomers which are used in making the polymers of the invention are low molecular weight polymers of esters of acrylic or methacrylic acid which have an allyl group in the ester residue. Generally, the oligomers will have a number average molecular weight of about 400 to about 10,000, and preferably about 700 to about 3000. The allyl-containing oligomers can be either homopolymers of allyl-containing esters or copolymers of allyl-containing esters with other esters of methacrylic acid or acrylic acid. However, the allyl-containing oligomers should have an average of at least about 3 allyl groups per molecule of the oligomer. Among the allyl-containing esters which can be used in making these oligomers are allyl acrylate, allyl methacrylate, allyloxyalkyl acrylates, preferably in which the alkyl group has 1 to 4 carbon atoms, including allyloxymethyl acrylate, allyloxyethyl acrylate, allyloxypropyl acrylate, and allyloxybutyl acrylate, allyloxyalkyl methacrylates, preferably in which the alkyl group has 1 to 4 carbon atoms, including allyloxymethyl methacrylate, allyloxyethyl methacrylate, allyloxypropyl methacrylate, and allyloxybutyl methacrylate, and the like. Mixtures of these esters can also be employed. Among the esters of methacrylic acid and acrylic acid which can be copolymerized with the allyl-containing esters are ($C_1$–$C_4$)alkyl methacrylates, preferably methyl methacrylate and ($C_1$–$C_8$)alkyl acrylates, including methyl acrylate, ethyl acrylate, butyl acrylate, and 2-ethylhexyl acrylate. Mixtures of these esters can also be employed.

Oligomers of any of the above allyl-containing esters can also be partially hydrolyzed before polymerization with the unsaturated acid to form an oligomer having carboxyl as well as allyl functionality. The hydrolysis can be carried out by any of the hydrolysis techniques which are well-known in the art. These partially-hydrolyzed oligomers are used in one of the preferred embodiments of the invention.

The oligomers used in making the polymers of the invention can be prepared by any convenient oligomerization technique. These allyl-containing oligomers can be prepared either by the direct polymerization of an allyl-containing monomer or by the transesterification of an oligomer of an alkyl acrylate or alkyl methacrylate with an allyl-containing alcohol, such as allyl alcohol or an allyloxyalkyl alcohol. In a preferred embodiment of the invention, the methacrylate oligomers are prepared by the procedures described in U.S. Pat. application Ser. No. 137,057, filed on Apr. 23, 1971, by S. N. Lewis and R. A. Haggard, entitled "Novel Polymers of Alkyl Methacrylates," now abandoned, and the continuation-in-part applications derived therefrom, Ser. No. 371,921 filed on June 20, 1973, now abandoned; Ser. No. 517,334 filed Oct. 23, 1974 now U.S. Pat. No. 4,059,616 issued Nov. 22, 1977; and Ser. No. 830,717 filed Sept. 6, 1977 now U.S. Pat. No. 4,133,793 issued Jan. 9, 1979 and the acrylate oligomers are prepared by the procedures described in U.S. Pat. application Ser. No. 241,177, filed on Apr. 5, 1972, now abandoned in favor of Ser. No. 629,186 filed on Nov. 5, 1975, by S. N. Lewis and R. A. Haggard, entitled "Novel Polymers of Alkyl Acrylates." A preferred class of methacrylate oligomers includes those in which the oligomer is an unhydrolyzed or partially-hydrolyzed anionically-polymerized polymer of allylmethacrylate or a ($C_3$–$C_7$)allyloxyalkylmethacrylate wherein the average chain length of the anionically-polymerized polymer is about 6 to about 50 mers, and wherein at least about 85% of the molecules of the anionically-polymerized polymer have chain lengths of about $\sqrt{2\bar{n}}$ to about $2\bar{n}$ mers, wherein $\bar{n}$ represents the average chain length of the anionically-polymerized polymer. A preferred class of acrylate oligomers includes those in which the oligomer is an unhydrolyzed or partially-hydrolyzed anionically-polymerized polymer of allyl acrylate or a ($C_3$–$C_7$)allyloxyalkyl acrylate wherein the average chain length of the anionically-polymerized polymer is about 6 to about 30 mers, and wherein at least about 80% by weight of the anionically-polymerized polymer consists of molecules having chain lengths of about $\bar{n}/3$ to about $3.3\ \bar{n}$ mers, wherein n represents the average chain length of the anionically-polymerized polymer. Oligomers prepared by other procedures, such as free-radical polymerization, can also be used.

In preparing the polymers of the invention, generally about 0.1% to about 10% by weight, and preferably about 0.5% to about 4% by weight, of the oligomer is used. Other monomers can be copolymerized with the oligomer and the carboxylic acid, including alkyl esters of methacrylic acid and acrylic acid, such as methyl methacrylate, ethyl acrylate, butyl acrylate, and the like, styrene, vinyl chloride, and functional monomer, such as maleic anhydride, sulfoethyl methacrylate, and the like. Generally, at least about 30% by weight of the polymer, preferably at least about 90%, and most preferably at least about 97% by weight, of the polymer, will be acid.

A wide variety of polymerization techniques can be used in preparing the polymers of the invention, and substantially any technique which will allow for easy isolation of the polymer will be appropriate. Among the suitable techniques are free-radical polymerization, including thermal and redox techniques, emulsion polymerization, non-aqueous dispersion polymerization, and the like.

A preferred technique is free radical polymerization in a solvent in which the acid and the oligomer are somewhat soluble, but in which the polymer produced is substantially insoluble. Among the solvents which can be used are benzene, toluene, xylene, hexane, heptane, methyl chloride, methylene chloride, ethylene chloride, tetrachloroethylene, t-butanol, and the like. The preferred solvents for this procedure are benzene and methylene chloride.

The free radical polymerization reaction is generally carried out in an inert atmosphere in the presence of a suitable free radical catalyst at a temperature of about 35° to about 80° C., preferably about 40° to about 50° C. Among the catalysts which can be used are peroxygen compounds, such as sodium, potassium and ammonium persulfates, caprylyl peroxide, benzoyl peroxide, hydrogen peroxide, pelargonyl peroxide, cumene hydroperoxides, tertiary butyl diperphthalate, t-butyl hydroperoxide, tertiary butyl perbenzoate, t-butyl peroxypivalate, sodium peracetate, sodium percarbonate, and the like, as well as azoisobutyronitrile, and the like. Other useful catalysts include the various redox catalysts and heavy metal activated catalyst systems. The amount of catalyst can vary, but generally about 1 to about 3% by weight is preferred. While the polymerization reaction is generally carried out at atmospheric pressure, it can also be carried out in a closed vessel under autogenous or induced pressure.

The polymers of the invention are particularly useful as thickening or bodying agents, for example, in cosmetics, shampoos, toothpastes, ointments, detergents, pigment printing compositions, polymer emulsions, including latex paints, oil well drilling compositions, and the like. The polymers also may be used as dispersants and lubricating oil additives. When used as thickening agents, the polymers are generally neutralized to a pH of about 4 to about 10, and preferably about 5 to about 8, and are thus present in the formulated composition in their partial salt form. In aqueous systems, the polymers are preferably neutralized with bases such as sodium, potassium, and ammonium hydroxides, carbonates, and bicarbonates, although other bases which are soluble in water can also be used. In non-aqueous systems, the polymers can be neutralized with organic bases, such as higher alkyl primary and secondary amines, which are themselves soluble in the system, to produce polymer salts which are soluble in the system, as well as with inorganic bases which are soluble in the system. Essentially any system, aqueous or non-aqueous, in which partially-neutralized polymers of the invention will dissolve will be thickened. As thickening agents, the polymers are generally used at concentrations of about 0.1% up to about 5% by weight, preferably about 0.5% to about 2% by weight, but higher or lower concentrations can be used to achieve particular thickening properties desired.

The following examples will further illustrate this invention but are not intended to limit it in any way. All parts are parts by weight and all temperatures are degrees Centigrade, unless otherwise stated.

EXAMPLE 1

Preparation of Allyl Methacrylate Oligomer (I)

A two-liter, three-necked flask equipped with a stirrer, thermometer, reflux condenser, gas inlet tube, and addition funnel is flushed with nitrogen and charged under nitrogen with 8.4 g. (0.075 mole) potassium t-butoxide, 29.0 g. (0.5 mole) allyl alcohol and 50.0 g. toluene. The mixture is heated to 60°±2° and 189 g. (1.5 moles) of allyl methacrylate are added over a 30 min. period after which the mixture is stirred at 60° for 3 hours. A solution of 441 g. (3.5 moles) allyl methacrylate in 65 g. of toluene is added over a 50 to 60 min. period and an exothermic reaction observed. The temperature is maintained at 60°±2° by cooling. Fifteen minutes after completion of addition, monomer is depleted as measured by vapor phase chromatography (vpc.). The mixture is cooled, neutralized with 4.8 g. (0.048 mole) of 98% sulfuric acid and charged with 3.9 g. of Hyflo Super-Cel filter aid and filtered through a pressure filter to give an 85.2% solids solution in toluene. The product is a yellow oil $\overline{M}_n$ 1120, $\overline{M}_w$ 1580 by gel permeation chromatography (gpc.).

EXAMPLE 2

Preparation of Acid-Containing Allyl Methacrylate Oligomer

A 250 ml., three-necked flask with a stopcock in the bottom is fitted with a mechanical stirrer, thermometer, and reflux condenser and charged with 88.9 g. of the oligomer of Example 1 and 24.8 g. of aqueous potassium hydroxide (8.13 meq. KOH/g.). The mixture is heated at 40° for one hour, 60° for two hours, and then at 80° for thirteen hours. The solution is cooled to 50° and 49.4 g. of phosphoric acid (4.14 mmol/g.) is added before dilution with 22 g. of toluene. After stirring well for fifteen minutes, the lower aqueous layer, which contains the bulk of the phosphate, is separated. The remaining water is removed by azeotropic distillation via a Dean-Stark trap over a two hour period. Traces of phosphate salts are removed by pressure filtration to give a clear, light yellow, 68.5% solids product containing 1.57 meq/g. of acid.

EXAMPLE 3

Preparation of Allyl Methacrylate Oligomer (II)

This example shows the preparation of an allyl methacrylate oligomer having an average molecular weight different from the oligomer of Example 1.

A one-liter, three-necked flask equipped with a mechanical stirrer, thermometer, addition funnel and reflux condenser attached to a nitrogen inlet tube is charged under nitrogen with 11.2 g. (0.1 mole) potassium t-butoxide and 100.0 g. of toluene. The slurry is heated to 75° and a solution of 504 g. (4 moles) of allyl methacrylate and 23.2 g. (0.4 mole) of allyl alcohol is added over a two-hour period while the temperature is maintained at 75°±2°. After completion of addition, the temperature is maintained an additional two hours and the mixture is then cooled to 60° and acidified with 5.3 g. (0.053 mol) of 98% sulfuric acid. Filtration through Hyflo Super-Cel filter aid in a heated pressure funnel gives an 85.5% solids yellow oil in toluene.

This oligomer is then hydrolyzed to give an acid-containing allyl oligomer by the following procedure.

A one-liter, three-necked flask with a bottom stop cock, mechanical stirrer, thermometer and reflux condenser is charged with 318.3 g. of the allyl methacrylate oligomer of Example 3 and 98.5 g. of aqueous potassium hydroxide containing 8.12 meq. KOH/g. The mixture is heated at 40° for one hour, 60° for two hours and 80° for three hours before cooling to 50° and acidifying with 211 g. of phosphoric acid solution containing 4.14 mmol/g. After addition of 100 g. of toluene, the aqueous layer is separated and the remaining water is removed by azeotropic distillation. Removal of traces of insoluble phosphate salts by pressure filtration provides a clear, light yellow, 81% solids product containing 2.05 meq. acid/g.

EXAMPLE 4

Preparation of Allyl Acrylate Oligomer

A 500 ml., three-necked flask equipped with a stirrer, thermometer reflux condenser, addition funnel and nitrogen inlet is flushed with nitrogen and 6.7 g. (0.06 mole) of potassium t-butoxide and 42.3 g. of toluene are added. Beginning at room temperature, 168.3 g. (1.5 moles) of allyl acrylate are added over a one-hour period. An exotherm raises the temperature to 70° within fifteen minutes. Heat is applied to keep the temperature at 70° throughout the addition. The color changes to yellow, orange and finally red. After maintaining the temperature at 70° for an additional 9 hours, vpc indicates good monomer conversion. The solution is cooled and 3.2 g. of concentrated sulfuric acid (63 meq.) is added to give a pale yellow, hazy product. Filtration provides a clear solution which is stripped at 100°/0.5 mm. to provide a 100% solids product of $\overline{M}_n$ 520, and Gardner-Holdt viscosity C.

EXAMPLE 5

Polymerization of Allyl Methacrylate Oligomer and Acrylic Acid

A mixture of 99.0 g. of acrylic acid and 1 g. of the oligomer of Example 1 in one liter of benzene is placed in a 2-liter, three-necked flask equipped with a stirrer, condenser, thermometer, and nitrogen inlet. Nitrogen is allowed to sweep over the solution for ten minutes. Two grams of azobisisobutyronitrile are added and the mixture is heated to 50°. After about 1.5 hours a precipitate begins to form and the solution begins to thicken. After 8.0 hours at 50°, the thick suspension is cooled and filtered. The solid cake containing a large amount of benzene is placed in a vacuum oven at 50° for 12 hours to give 97.5 g. of a fluffy white solid.

EXAMPLE 6

Polymerization of Partially-Hydrolyzed Allyl Methacrylate and Acrylic Acid

To a 2-liter, three-necked, round-bottomed flask equipped with a stirrer, condenser, thermometer, and nitrogen inlet is added one liter (1316 g.) of methylene chloride, 98.25 g. of acrylic acid, and 2.5 g. of the oligomer of Example 2 (1.75 g. of 100% solids). The mixture is stirred and nitrogen gas swept through system for ten minutes. Two grams of azobisisobutyronitrile is added and the mixture heated to reflux with a very slow nitrogen flow. The solution begins to get hazy within about five minutes of reaching the reflux temperature (41°). The mixture is allowed to reflux for 8.0 hr. and the solid which precipitated is collected on a centrifuge and dried overnight in a vaccum oven at 50°. The resulting fluffy white powder weighed 98.7 g.

EXAMPLE 7

Polymerization of Acrylic Acid and Allyl Acrylate Oligomer

The polymer is prepared following the procedure of Example 6 from 99 g. of acrylic acid and 1 g. of the allyl acrylate oligomer of Example 4 in one liter of methylene chloride. After 8.0 hours of reflux, the product is collected on a filter and dried in a vacuum oven for 12 hours to give 98.6 g. of product.

The following three examples show the use of polymers of the invention as thickening agents in water.

EXAMPLE 8

A 1 g. sample of the polymer of Example 5 is put into 100 g. of water and the mixture is stirred by means of a technical stirrer for one hour at which time the solid is well dispersed. To this solution, pH 2–3, is added 10% NaOH with stirring. Viscosity builds rapidly and thickening is measured with a Brookfield viscometer, spindle no. 4 at 6 RPM. Viscosity exceeds 100,000 cps at pH 4.3. When methacrylic acid is substituted for acrylic acid in the polymer of Example 5, similar thickening effects are obtained.

EXAMPLE 9

A mixture of 1 g. of the polymer of Example 6 and 199 g. of water is agitated for one hour. The hazy mixture is made gradually basic. The following list shows the extent of thickening at various pH levels.

| pH | Viscosity | Appearance |
|---|---|---|
| 2.7 | 2,000 cps | hazy |
| 5.4 | >100,000 cps | clear |
| 6.5 | >100,000 cps | clear |
| 7.5 | >100,000 cps | clear |
| 8.2 | >100,000 cps | clear |
| 12.0 | 70,000 cps | clear |

EXAMPLE 10

A suspension of 1 g. of the polymer of Example 7 in 99 g. of water is thickened by slow addition of 10% NaOH. The following list shows the extent of thickening of various pH levels.

| pH | Viscosity (No.4, 6rpm) | Appearance |
|---|---|---|
| 2.2 | 10,000 | hazy |
| 4.7 | 61,000 | clear |
| 5.5 | 72,500 | clear |
| 6.3 | 76,000 | clear |
| 7.2 | 75,000 | clear |
| 8.1 | 73,000 | clear |

EXAMPLE 11

Preparation of 2-Allyloxyethyl Methacrylate Oligomer

To a 1-liter, 3-necked, round-bottomed flask equipped with a mechanical stirrer, thermometer, Y-tube adaptor, addition funnel, and reflux condenser connected to a dry nitrogen inlet is charged with 3.36 g. (0.03 mole) potassium tert-butoxide, 20.0 g. (0.20 mole) 2-allyloxyethanol, and 30 g. of toluene. The mixture is heated to 60° and 102 g. (0.6 mole) of 2-allyloxyethyl methacrylate is added over a period of 25 minutes. Maintaining the reaction mixture at 60°, the solution is checked periodically for conversion of monomer to pre-oligomer. After 6 hours, a large amount of monomer remains. The mixture is cooled and maintained under nitrogen overnight.

The reaction mixture is charged with an additional 3.36 g. (0.03 mole) potassium tert-butoxide and heated to 80°. After 30 minutes the mixture is much darker in color and gas-liquid chromatographic (glc) analysis indicates near quantitative conversion of 2-allyloxyethyl methacrylate to pre-oligomer. The pre-oligomer solution is cooled to 60°. A solution of 238 g. (1.4 mole) 2-allyloxyethyl methacrylate and 33 g. of toluene is added over a 45-minute period. Oligomer growth is exothermic with cooling frequently necessary to maintain the 60° reaction temperature. Thirty minutes after monomer addition, glc analysis indicates essentially quantitative conversion of monomer to oligomer. The mixture is neutralized with 3.0 g. (0.3 mol) of 98% sulfuric acid. The precipitate is allowed to settle and the supernatent polymer solution is decanted. The product is a yellow oil at 84.0% solids.

EXAMPLE 12

Preparation of Acid-Containing 2-Allyloxyethyl Methacrylate Oligomer

To a 500 ml., round bottomed, 3-necked flasked modified with a bottom stopcock and equipped with a mechanical stirrer, thermometer, and reflux condenser is charged 181 g. (0.873 mole) of the oligomer of Example 11 (84.0% solids) and 43.5 g. (0.349 mole) of 45.0% aqueous potassium hydroxide. The mixture is heated at 40° for 1 hour, 60° for 2 hours, and at 80° for 5½ hours to give an 80% conversion of potassium hydroxide to carboxylate anion. The reaction mixture is then diluted with toluene, and acidified with 84.5 g. (0.349 mole) of 40.5% aqueous phosphoric acid. After a slow separation, the aqueous layer was removed. The mixture is transferred to a 3-l., round bottomed, 3-necked flask equipped with a mechanical stirrer, diluted with 1400 ml. of diethyl ether, and extracted with 6×300 ml. portions of water. Ether is removed by distillation and traces of water are removed by azeotropic distillation with toluene at reduced pressure (250 mm., maximum pot temperature 70°). The warm reaction mixture is filtered through a Buchner funnel to give a clear yellow oil at 67.0% solids containing 1.50 meq. acid/g. solution. Glc analysis of the product shows less than 0.5 wt.% of 2-allyloxyethanol.

EXAMPLE 13

Polymerization of 2-Allyloxyethyl Methacrylate Oligomer and Acrylic Acid

To a 2-l., 3-necked, round-bottomed flask equipped with a stirrer, condenser, thermometer, and nitrogen inlet are added 1316 g. of methylene chloride, 1.0 g. sodium dodecylbenzene sulfonate 144.5 g. of acrylic acid 1.74 g. of the oligomer of Example 11. The mixture is stirred and swept with nitrogen. After ten minutes, 2.9 g. of azobisisobutyronitrile is added and the mixture is heated to reflux and held at this temperature for eight hours. The solid which begins to precipitate early in the reaction is collected on a filter and dried in a vacuum oven at 50° to give 142.3 g. of product.

This polymer has the following thickening efficiency at 0.5% in water at various pH levels;

| pH | Viscosity (cps) No. 4/6 RPM | Appearance |
|---|---|---|
| 2.2 | 3,000 | sl. haze |
| 5.5 | 36,000 | very sl. haze |
| 7.0 | 44,000 | very sl. haze |
| 9.2 | 48,000 | very sl. haze |

Following the procedure described above, using 98.25 g. of acrylic acid and 2.1 g. the oligomer of Example 11 in 1316 g. of methylene chloride with 2.0 g. of AIBN initiator, 96 g of product was obtained which had the following thickening efficiency at 0.5% in water at various pH levels:

| pH | Viscosity (cps) no. 4/6 RPM | Appearance |
|---|---|---|
| 2.2 | 100 | hazy |
| 5.4 | 82,000 | sl. haze |
| 6.4 | >100,000 | sl. haze |
| 7.6 | >100,000 | sl. haze |
| 11.6 | >1,000 | sl. haze |

EXAMPLE 14

Polymerization of Acid-Containing Allyloxyethyl Methacrylate Oligomer and Acrylic Acid The procedure of Example 13 is followed employing 1316 g. of methylene chloride. 1.0 g. of sodium dodecyl benzene sulfonate, 143.5 g. of acrylic acid 3.7 g. of the oligomer of Example 12 and 0.58g. of Lupersol 11 initiator. The product weight is 135 g. and the thickening efficiency of the product at 0.5% in water is shown below.

| pH | Viscosity (cps) No.4/6 | Appearance |
|---|---|---|
| 2.1 | 100 | hazy |
| 5.6 | 46,000 | sl. haze |
| 6.6 | 54,000 | sl. haze |
| 7.6 | 59,000 | sl. haze |
| 11.5 | 15,000 | sl. haze |

The following two examples show typical use formulations comprising thickening agents of the invention:

EXAMPLE 15

Shampoo Thickener (General Formulation)

To thirty parts of sodium lauryl sulfate (30% solution) in 69 parts of water is added 1 part of a polymer of Example 5, 6, or 7. The mixture is stirred to disperse the polymer and the pH was adjusted by addition of 25% aqueous sodium hydroxide.

|  | Polymer | Polymer |
|---|---|---|
| pH | 6.9 | 7.8 |
| Viscosity (No.4,60rpm) | 2550 cps | 1950 cps |

EXAMPLE 16

Pigment Printing Paste Thickeners

Clear thickened pastes are prepared by addition of polymer to water in the amounts described. The powders are dispersed by mechanical stirring and the pH is raised to 8.7 by addition of 28% NH$_4$OH.

|  | Clear 0.7% | Clear 1.0% |
|---|---|---|
| H$_2$O | 99.3 g. | 99.0 |
| Polymer | 0.7 g. | 1.0 |
| Viscosity (No.4,6rpm) | >100,000 cps | >100,000 cps |

The clears are used to thicken print pastes as follows:

| | | | |
|---|---|---|---|
| Print Paste | 0.7% | Print Paste | 1.0% |
| Blue Pigment | 10.0 | | 10.0 |
| Rhoplex E-32 | 10.1 | | 10.1 |
| NH₄NO₃ (25%) | 2.0 | | 2.0 |
| Clear | 77.9 (0.7% clear) | | 77.9 (1% clear) |
| Viscosity | | | 45,000 cps |
| (No.4,6rpm) | 13,000 cps | | |

The following four examples show the application of polymers of the invention as thickening agents for various nonaqueous and partially nonaqueous systems.

EXAMPLE 17

To 100 parts of propylene glycol is added two parts of the polymer of Example 6. The mixture was stirred until the polymer dissolved to give a thickened mix of 42,000 cps viscosity.

EXAMPLE 18

To 100 parts of polyethylene glycol (Carbowax 600) is added two parts of the polymer of Example 6. The mixture is stirred until the polymer dissolves to give a viscosity over 100,000 cps.

EXAMPLE 19

To a mixture of 50 parts water and 50 parts isopropanol is added 1 part of the polymer of Example 6. The pH is adjusted to 6.5 with 1 part of triethanolamine and the mixture becomes thick. A viscosity of 87,000 cps is observed.

EXAMPLE 20

To a mixture of 100 parts of methanol and 1 part of the polymer of Example 6 is added ammonium hydroxide. The measured pH of the system is 6.2 and the viscosity is 16,5000 cps.

It is to be understood that changes and variations may be made without departing from the spirit and scope of the invention as defined by the appended claims.

We claim:

1. A method of thickening a liquid composition which comprises dissolving in the composition a solid polymer of a polymerizable mixture comprising: (A) at least about 30% by weight, of the polymer, of a monoethylenically $\alpha,\beta$-unsaturated carboxylic acid selected from acrylic acid, methacrylic acid, ethacrylic acid, $\alpha$-chloroacrylic acid, crotonic acid, itaconic acid, maleic acid, fumaric acid, citraconic acid, mesaconic acid and mixtures of same, and (B) an oligomer having a number average molecular weight of from about 400 to about 10,000, wherein the oligomer is an unhydrolyzed or partially-hydrolyzed anionically-polymerized oligomer of allyl methacrylic or a (C₃–C₇)allyloxyalkyl methacrylate; wherein the average chain length of the oligomer, $\bar{n}$, is about 6 to about 50 mers and at least about 85% of the molecules have chain lengths of about $\sqrt{2\bar{n}}$ to about $2\bar{n}$ mers and wherein the oligomer comprises about 0.1% to about 10% by weight of the mixture; in an amount effective to cause thickening.

2. A method according to claim 1 wherein the oligomer is an oligomer of allyl methacrylate having a number average molecular weight between about 700 and about 3,000; the polymer is neutralized to a pH of about 4 to about 10; and the acid is acrylic acid.

3. A method according to claim 2 wherein the liquid composition is an aqueous composition.

4. A method according to claim 2 wherein the polymer is dissolved in the composition in an amount of about 0.1% to about 5% by weight.

5. A thickened composition which comprises the polymer of claim 2 and a solvent.

6. A composition according to claim 5 wherein the solvent is water and the polymer is dissolved in the composition in an amount of about 0.1% to about 5% by weight.

7. A method of thickening a liquid composition which comprises dissolving in the composition a solid polymer of a polymerizable mixture comprising: (A) at least about 30% by weight, of the polymer, of a monoethylenically $\alpha,\beta$-unsaturated carboxylic acid selected from acrylic acid, methacrylic acid, ethacrylic acid, $\alpha$-chloroacrylic acid, crotonic acid, itaconic acid, maleic acid, fumaric acid, citraconic acid, mesaconic acid and mixtures of same, and (B) an oligomer having a number average molecular weight of from about 400 to about 10,000, wherein the oligomer is an unhydrolyzed or partially-hydrolyzed oligomer of allyl acrylate or a (C₃–C₇)allyloxyalkyl acrylate; wherein the average chain length of the oligomer, $\bar{n}$, is about 6 to about 30 mers and at least about 80% by weight consists of molecules having chain lengths of about $\bar{n}/3$ to about $3.3\bar{n}$ mers and wherein the oligomer comprises about 0.1% to about 10% by weight of the mixture; in an amount effective to cause thickening.

8. A method according to claim 7 wherein the oligomer is an oligomer of allyl acrylate having a number average molecular weight between about 700 and about 3,000; the polymer is neutralized to a pH of about 4 to about 10; and the acid is acrylic acid.

9. A method according to claim 8 wherein the liquid composition is an aqueous composition.

10. A method according to claim 8 wherein the polymer is dissolved in the composition in an amount of about 0.1% to about 5% by weight.

11. A thickened composition which comprises the polymer of claim 8 and a solvent.

12. A composition according to claim 11 wherein the solvent is water and the polymer is dissolved in the composition in an amount of about 0.1% to about 5% by weight.

* * * * *